United States Patent
Stanford

[19]

[11] Patent Number: 6,027,519

[45] Date of Patent: Feb. 22, 2000

[54] CATHETER WITH EXPANDABLE MULTIBAND SEGMENT

[76] Inventor: Ulf Harry Stanford, 2023 Eagle Ct., Santa Rosa, Calif. 95403

[21] Appl. No.: 09/208,715

[22] Filed: Dec. 9, 1998

Related U.S. Application Data

[60] Provisional application No. 60/069,462, Dec. 15, 1997, abandoned.

[51] Int. Cl.[7] .................................................. A61M 29/04
[52] U.S. Cl. ......................... 606/198; 606/194; 606/192; 604/96
[58] Field of Search ............................... 606/1, 159, 192, 606/194, 195, 198; 604/96–101; 623/1, 12

[56] References Cited

U.S. PATENT DOCUMENTS 5,690,643  11/1997  Wijay ...................................... 606/198
5,769,871  6/1998  Kelly et al. ............................. 606/194

*Primary Examiner*—Michael Buiz
*Assistant Examiner*—William W. Lewis
*Attorney, Agent, or Firm*—Bruce H. Johnsonbaugh

[57] ABSTRACT

A catheter is provided for use in blood vessels and other body canals having one or more expandable segments. Each expandable segment includes a plurality of longitudinally extending bands, each band having a plurality of buckle points so that, as compressive axial forces are applied, the bands bend at the buckle points in a predetermined manner to expand outwardly. Fluid passageways are provided to apply the necessary axial compressive forces. A flexible resilient membrane encloses the expandable section and retracts the section so that the catheter may be withdrawn. The catheter is usable with or without stents. Multiple expandable segments may be utilized on the catheter for multi-tasking such as pre-expanding an artery and inserting one or two stents in the pre-expanded artery in a single procedure without withdrawing the catheter.

15 Claims, 12 Drawing Sheets

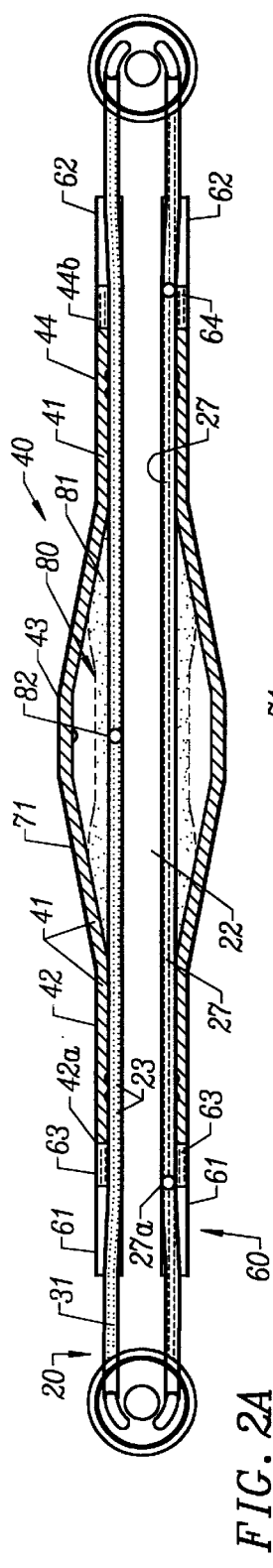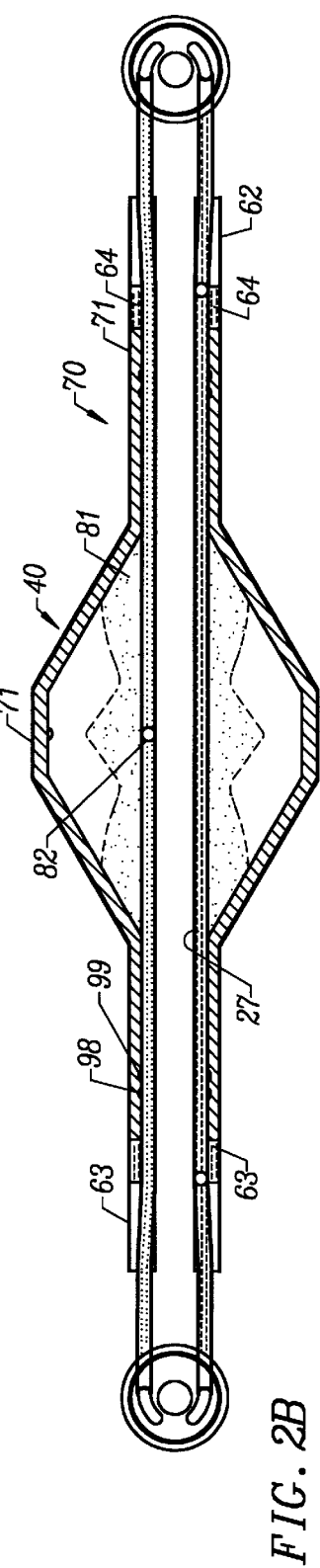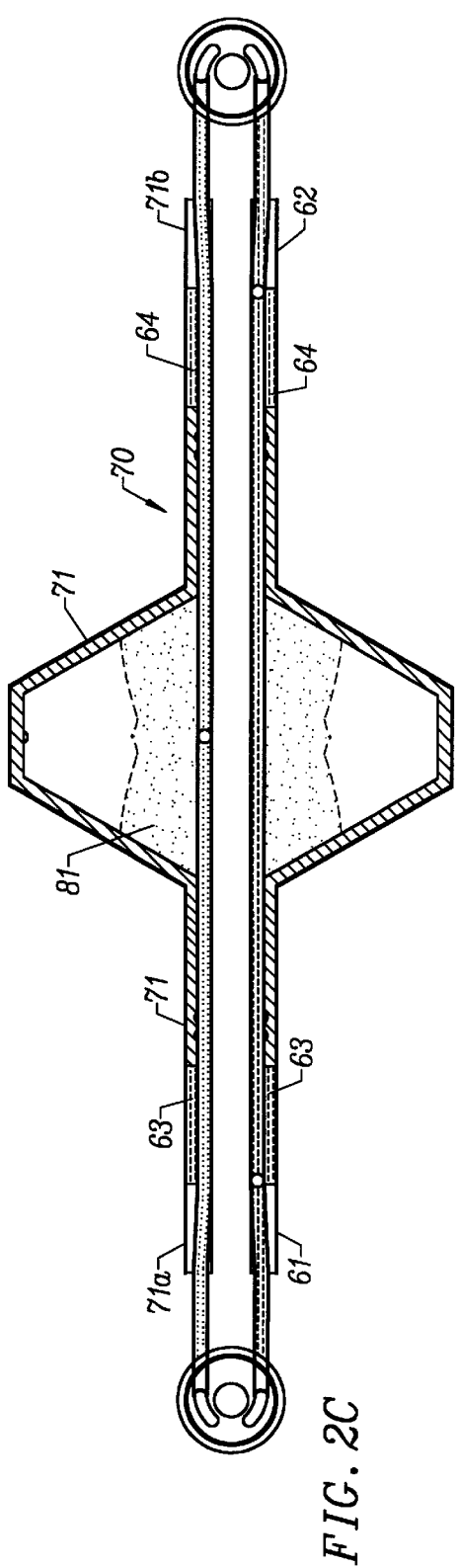

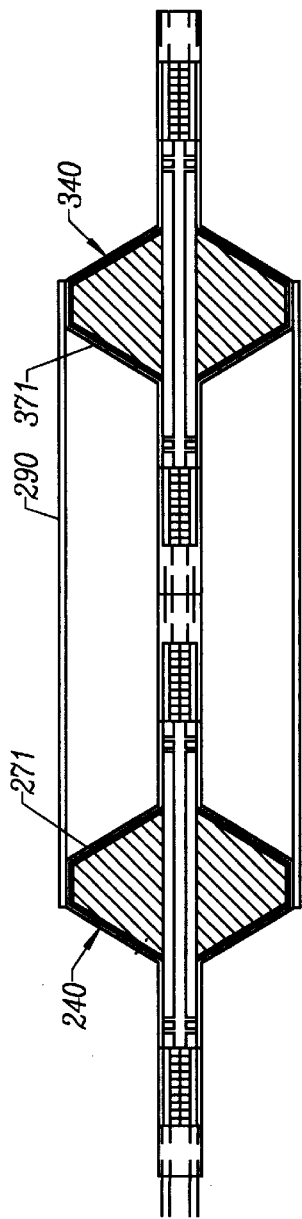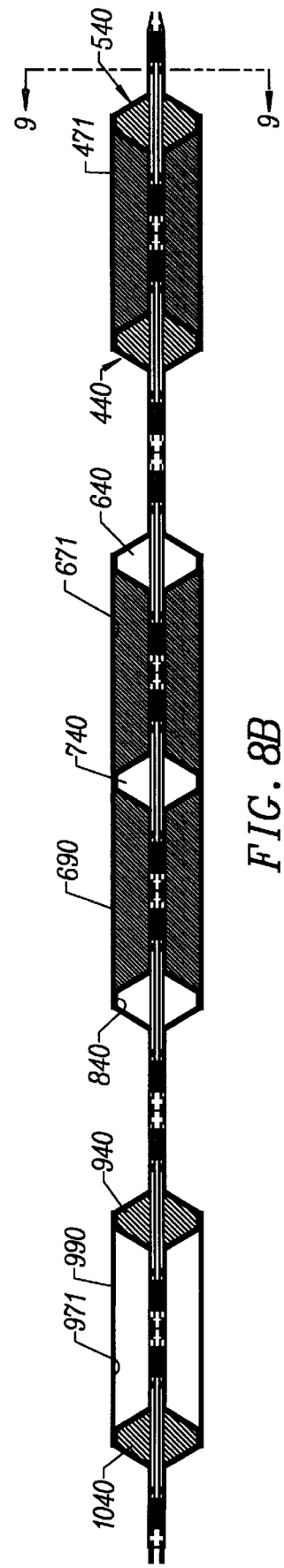

CATHETER WITH EXPANDABLE MULTIBAND SEGMENT

CROSS-REFERENCE TO RELATED APPLICATION

This application claims the benefit of United States provisional application Serial No. 60/069,462 filed Dec. 15, 1997, now abandoned.

BACKGROUND AND BRIEF SUMMARY OF THE INVENTION

The present invention relates generally to catheters for use in blood vessels or other body canals. More particularly, the present invention relates to a catheter having a "non-balloon" expandable segment wherein the expandable segment is actuated by the use of compressive forces applied to a series of bands which deform in a predetermined fashion, thereby expanding to an infinite number of diameters. The present invention may be used to implant stents but, also, has a variety of uses wherein a stent is not utilized in the procedure.

The prior art includes balloon catheters as well as the Krumme U.S. Pat. No. 5,409,460 which relates to a non-balloon expander assembly.

The Krumme patent teaches a system having several serious drawbacks. First, the patent discloses an expander assembly having a core element sensitive to temperature changes and the expansion is caused by the application of heat to electrical resistance elements which in turn heat the metal. The application of heat and electrical voltage inside the lumen creates a variety of possible adverse medical complications. Furthermore, the Krumme design is incapable of use with a guide wire. As a practical matter, incapability with a guide wire renders the device practically useless in coronary vessels and the device shown in the Krumme patent has not been built or commercialized.

The prior art also includes balloon catheters. Balloon catheters are well-known medical devices with an inflatable balloon attached to the distal end of a catheter. Positioning and inflation of the balloon within a body space (usually a vessel) results in dilation of the body space. Over the last twenty years, balloon catheters have become widely accepted for use in a medical procedure called Percutaneous Transluminal Coronary Angioplasty (PTCA), first introduced by Andreas Gruent-zig in 1977. Balloon catheters for angioplasty are typically made out of thin walled, high tensile strength materials with relatively low resilience. The materials used in angioplasty are flexible with varying degrees of elasticity (compliance). The noncompliant balloon will readily inflate to a predetermined diameter at normal pressures. The more compliant balloon allows some flexibility in diameter achievement.

The success of the angioplasty procedure has, unfortunately, included some significant and life threatening problems. Patients with arteriosclerotic disease who undergo balloon angioplasty are at risk for abrupt vessel closure and acute dissection. In the event of a partial or total occlusion of a coronary artery from a blood clot or from dissection of the arterial lining, the patient's life may be jeopardized. Immediate medical intervention often is required. Even if angioplasty is initially successful, as many as 40% of many patients experience restenosis of the treated artery.

Due to the above problems, recent efforts have led to the development of endoprosthetic devices, commonly called stents. Stents are metallic cylindrical devices, deployed by a balloon in the artery at the lesion location in order to maintain the artery's patency. Today, the most commonly used stent delivery system was developed by Johnson & Johnson International Systems. This system, which is based on conventional balloon catheter technology, disposes a balloon expandable stent crimped onto a folded, non-inflated balloon. The catheter is introduced percutaneously through the femoral artery into the patient's cardiovascular system until the stent is located at the lesion site. Balloon inflation causes the stent to expand and dilate the artery. The final step in the procedure is to deflate the balloon and to retract the catheter, leaving the stent in place. Since the stent is designed such that it will not compress once it expands, the artery is held open by the radial strength of the stent.

Although the use of a stent overcomes some of the problems associated with angioplasty, the use of balloon catheter technology to expand the stent has resulted in other potential complications, which may arise during implantation of the stent:

1. As the balloon inflates to expand the stent, the distal end of the balloon inflates outside the longitudinal boundary of the stent, potentially resulting in serious damage to the artery.

2. If the balloon, which is typically very thin walled, develops a leak, the balloon material may result in incomplete stent deployment and may make catheter extraction more difficult.

3. Lack of uniform unfolding of the balloon may result in a asymmetrical expansion and incomplete dilation.

4. The stent may slide off the balloon and embolize distally making extraction difficult and exposing the patient to serious, life threatening consequences.

Another significant limitation in the use of a balloon catheter to deploy a stent results from the need to determine precisely the correct stent diameter to be used for the procedure. Often additional balloons are required to achieve the correct stent expansion.

In short, surgeons need a stent delivery and removal apparatus and system that overcomes the limitations of the balloon catheter system by providing a system which is safer, more efficient, less wasteful, and provides the surgeon with a range of procedural options which do not exist with the current stent delivery technology.

The present invention provides a new and unique catheter design that avoids the limitations inherent in the design of the Krumme U.S. Pat. No. 5,409,460 and which avoids the problems associated with the conventional balloon catheters as used either with or without stents. In general, the present invention is capable of use with guide wires and does not require the application of heat to the expander, the use of special heat sensitive alloys or the use of electrical voltages inside the lumen. The present invention utilizes an expandable segment having a plurality of longitudinally extending bands wherein each of the bands has a plurality of predesigned buckle points. When compressive axial forces are applied to the bands, the bands expand at the buckle points. The bands may be expanded to an infinite variety of diameters, in sharp contrast to conventional balloon catheters.

The present invention also includes several advantages over the prior art when used in conjunction with a stent. For example, the present invention can deliver several stents of different lengths simultaneously. One or more of the stents can be implanted in a single procedure without removing the catheter to implant a second or third stent.

The invention also provides the surgeon with a more precise and flexible procedure for implanting stents in a patient's artery. Current balloon catheter technology requires the surgeon to select a predetermined stent and balloon size. The balloon must completely inflate in order for the stent to expand properly. If the surgeon selects a stent having a diameter that is either too large or too small, problems can arise. If the expanded stent is too small, the likelihood for restenosis is greater. On the other hand, if the stent diameter is too large, the stent may cause serious damage to the artery. The present invention overcomes these problems by providing the physician with the means to expand the stent in a controlled manner and potentially over a larger range of stent diameters.

Another feature of the present invention includes a multi-tasking feature including a stent preparation segment and a separate stent delivery segment wherein the stent preparation segment is substantially identical to the stent delivery segment with the exception that a stent is not disposed around the tube. The stent preparation segment, when expanded at a lesion site, opens the artery in order to prepare the artery for insertion of the stent. The stent preparation segment may similarly be incorporated as part of a multi-tasking tube and, in a preferred embodiment, the stent preparation segment is located on the distal end of the tube. The tube may also contain a medication chamber, which may be expanded in a manner similar to the expansion of the stent delivery segment and, thereby, cause medicine to be released at a needed location within a body lumen.

Another feature of the present invention is that the stent delivery segment may be used to deliver other endoprosetic devices, such as stents of various expanded shapes and configurations to be used in tapered or asymmetrical body lumens. A particularly significant application is to use the invention to implant a stent-plug within an artery, which is providing blood to a cancerous tumor so as to block the supply of blood to the tumor, causing the tumor to die.

The above-described novel stent delivery apparatus and system has a particularly novel and useful application to its use in the surgical implantations of stents within a patient's cardiovascular system, because the invention overcomes some of the serious life threatening limitations of present balloon catheter stent implantation technology. It should be apparent that the present invention does not exhibit any of the problems associated with the use of a balloon, since the sealed balloon is replaced with an elongated tube having an expandable section. This expandable section expands symmetrically away from the tube's axis when a slight compressive force is applied to the tube in an axial direction. Thus, the stent cannot slide off the tube due to asymmetrical expansion. It should also be apparent that the invention cannot leak, like the balloon, because the unique stent apparatus and delivery system uses a physical force, rather than a radiocontrast material (fluid) to expand the stent.

The present invention differs from balloon catheters in the significant respect that, whereas balloon catheters require the use of relatively high pressure to expand the balloon, the present invention utilizes less than half the pressure, reducing the risk of rupturing or tearing the lumen wall.

Another significant advantage of the present invention is that the expansion segment has longitudinal flexibility and may be utilized in a curved portion of a blood vessel or other lumen. Prior art balloon catheters use relatively high pressure to expand the balloon and may involve significant risk when used in a curved artery or other lumen.

A primary object of the invention is to provide a catheter with a safer, more reliable and improved "non-balloon" expansion mechanism, as described above.

A further object is to provide a catheter with one or more expandable segments for use with or without stents, as described above.

Further objects and advantages will become apparent from the above summary and the following description and drawings, wherein:

BRIEF DESCRIPTION OF THE DRAWINGS

FIGS. 2A, 2B and 2C show the expandable segment in three different stages of expansion;

FIGS. 8A and 8B are side elevational views in section showing other embodiments of the invention;

DETAILED DESCRIPTION OF THE DRAWINGS

Figure 1:
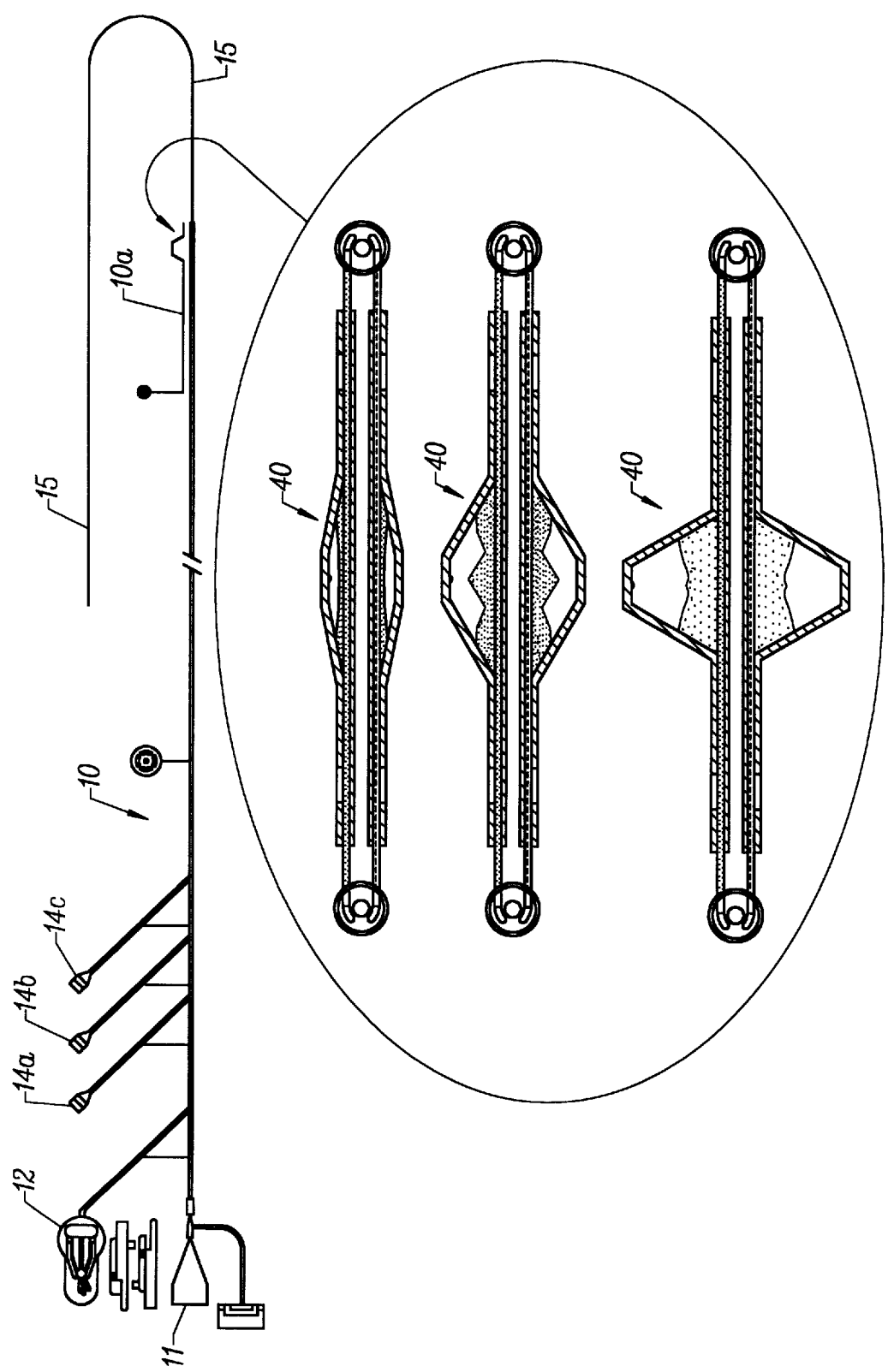
FIG. 1 is a schematic representation of the catheter of the present invention as placed upon a guide wire and which shows in the exploded insert how the expandable segment is positioned on the catheter and how it expands.
Figure 3:
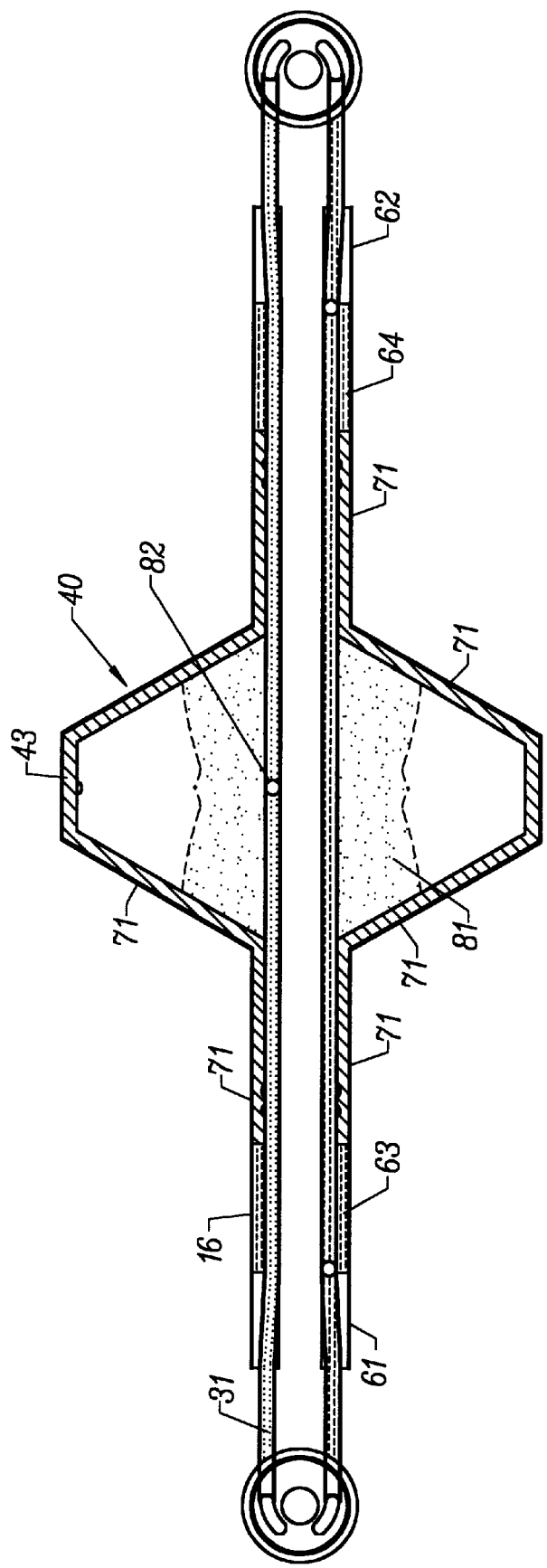
FIG. 3 is a sectional view of the expandable segment shown fully expanded.
Figure 4:
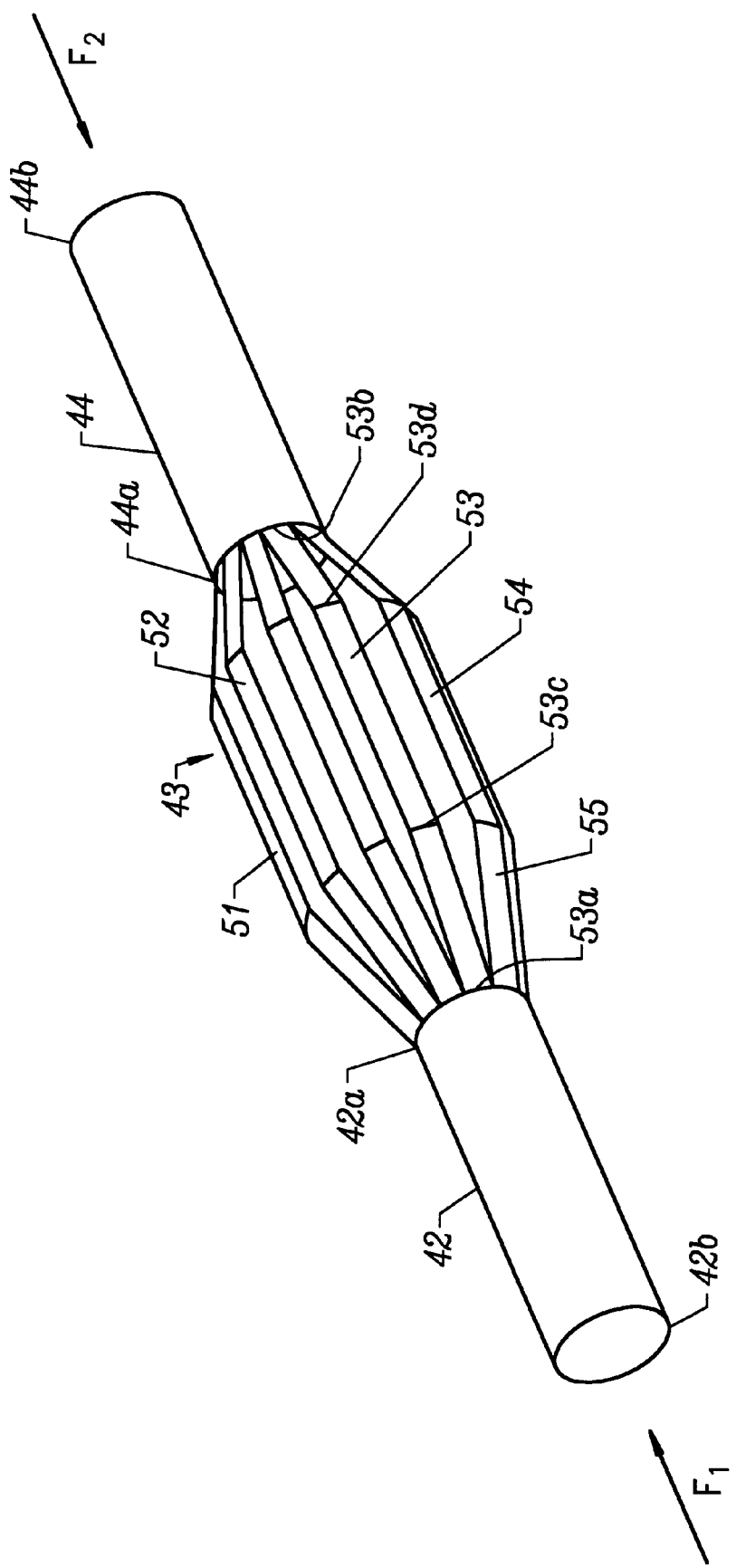
FIG. 4 is a perspective view showing the portion of the invention utilizing a plurality of bands which buckle in response to compressive axial forces.
Figure 5:
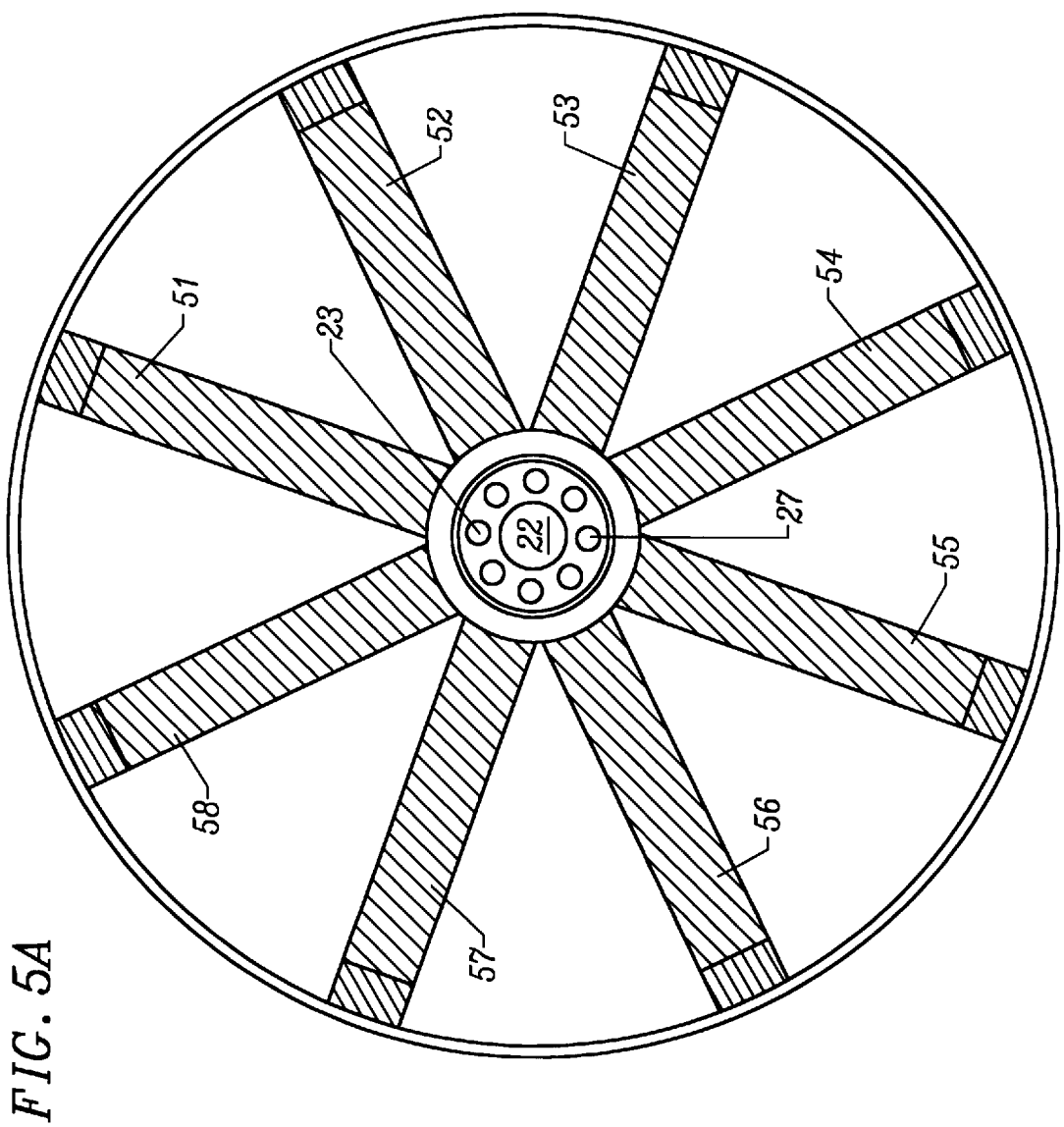
FIG. 5 is a front elevational view, partially in section, showing the expandable segment of FIG. 4 and showing the inner cylindrical member which carries the expandable segment.

FIGS. 1–5 show a first embodiment of the invention wherein a single expandable segment is utilized without a stent. As shown in FIG. 1, the catheter 10 is shown after having been slid onto a guide wire 15. The catheter 10 is connected to a guide wire controller 11 and a fluid control panel 12 which introduces radiographic contrast fluid as well as fluid for creating the necessary axial compressive forces to activate the expandable segment, as described below in greater detail. FIG. 1 also shows as 14a, 14b and 14c various optional fluid supply mechanisms which may be used to introduce medications and other fluids discussed in greater detail below.

Catheter 10 has a distal tip 10a which carries the expandable segment shown generally as 40 in the exploded insert of FIG. 1. The exploded insert shows expandable segment 40 in three separate stages of expansion, also shown in greater detail in FIGS. 2A, 2B and 2C.

As shown in FIGS. 2A, 2B and 2C, catheter 10 includes an inner elongated cylindrical member 20, the cross section of which is shown best in FIG. 5B. FIG. 5B shows the preferred embodiment of the inner elongated cylindrical member 20, which includes a cylindrical body 21 having a first cylindrical passageway 22 extending preferably along the central longitudinal axis of member 20 and is designed to slide onto guide wire 15 as shown in FIG. 1. The inner elongated cylindrical member 20 includes a series of eight passageways 23–30 formed within the wall thickness of cylinder 21 and which extend parallel to the first passageway 22 and parallel to the longitudinal axis of inner cylindrical member 20. As described in greater detail below, these eight passageways 23–30 form additional passageways which may be utilized for the introduction of radiographic contrast fluid, expansion fluid, medications and other fluids. Inner cylindrical member 20 has an exterior surface 31 which, in the embodiment shown in FIG. 5B, forms a circular smooth elongated cylinder.

As shown in FIGS. 2A–2C, the inner elongated cylindrical member 20 carries expandable segment 40. Expandable segment 40 includes an outer sleeve 41 which includes a proximal section 42, a mid section 43 and a distal section 44. The outer sleeve 40 is shown best in FIG. 4. Proximal section 42 is a smooth cylindrical cylinder having an inner end 42*a* adjacent mid section 43 and an outer end 42*b*, against which axial compressive forces are applied as described below. Distal section 44 is a smooth cylinder with circular cross section and is preferably identical to proximal section 42. Distal section 44 has an inner end 44*a* adjacent mid section 43 and an outer end 44*b*.

Mid section 43 includes a plurality of longitudinally extending bands 51–58, which extend between the inner ends 42*a* and 44*a* of proximal and distal sections 42 and 44.

Bands 51–58 each has four buckle points. For clarity, the buckle points will only be described for band 53, but it is understood that each of the bands is identical and each band has identical buckle points to band 53 in the preferred embodiment. Band 53 has a total of four buckle points including a first buckle point 53*a* at the point where the band 53 connects to the inner end 42*a* of proximal section 42. A second buckle point 53*b* is located at the point where band 53 connects the inner end 44*a* of proximal section 44. Third and fourth buckle points 53*c* and 53*d* are located between the first and second buckle points 53*a* and 53*b*. One of the significant variables of the invention is the placement of the buckle points along each longitudinal band 51–58. By placing the third and fourth buckle points closer to the first and fourth buckle points, the resultant expanded diameter of the expandable section 40 is reduced. Conversely, by moving the third and fourth buckle points 53*c* and 53*d* further away from the first and fourth buckle points 53*a* and 53*b*, the resultant outer diameter of the expanded segment 40 is increased. It is to be understood that in the preferred embodiment shown in FIG. 4, all of the first buckle points are coplanar and are oriented perpendicularly to the longitudinal axis of the expandable segment 40. Similarly, the second, third and fourth buckle points are all coplanar and perpendicular to the longitudinal axis. It is entirely within the scope of this invention to provide buckle points which are coplanar but are oriented angularly with respect to the longitudinal axis of the expandable segment 40. It is also within the scope of the invention to position the third and fourth buckle asymmetrically with respect to the first and second buckle points in order to generate an expandable segment 40 capable of expanding in various asymmetrical designs for various medical purposes. It is furthermore possible to use a different number of buckle points other than four for each of the longitudinal bands. For example, only three buckle points could be utilized wherein the expandable segment 40 would have a triangular cross section. However, the preferred embodiment of positioning of buckle points produces the trapezoidal cross section shown best in FIG. 2C when the expandable segment 40 is fully expanded.

Expansion means 60 is provided in order to produce and apply compressive axial forces to either or both of proximal section 42 and/or distal section 44. In the preferred embodiment, equal and oppositely oriented forces are applied as shown by arrows $F_1$ and $F_2$ in FIG. 4. In the embodiment shown in FIGS. 2A, 2B and 2C, first and second stop blocks 61 and 62 are affixed to the outer surface 31 of the inner cylindrical member 20. First and second fluid expansion chambers 63 and 64 are provided between stop blocks 61,62 and the outer ends 42*b* and 44*b* of proximal and distal sections 42 and 44. Expansion fluid enters chambers 63 and 64 through passageway 27 formed in inner cylindrical member 20 and through ports 27*a* and 27*b* to establish fluid communication between the second passageway 27 and expansion chambers 63 and 64. The fluid in passageway 27 is pressurized typically by a bladder pump 12 or other pumping mechanisms known in the art. As the expansion fluid flows through ports 27*a* and 27*b* and enters chambers 63 and 64, equal and opposite compressive axial forces $F_1$ and $F_2$ are applied to the expandable segment 40 and segment 40 bends in predetermined fashion at the buckle points described above and expands to an infinite number of diameters up to its point of full expansion as shown schematically in FIG. 2C. By applying equal and opposite axial forces, the expandable segment 40 expands without moving longitudinally relative to the wall of the vessel or other body canal. It is also possible to cause expansion of the segment 40 by applying a compressive force to only one of the distal or proximal sections, however, that approach is somewhat less preferred because there will be some resulting longitudinal motion of the expanding section.

A retraction means shown generally as 70 is provided for causing the mid section 43 to retract when the expansion fluid is no longer pressurized. Expansion means 70 in the preferred embodiment is a single continuous rubber membrane 71 having a distal end 71*a* which covers first stop block 61 and a distal end 71*b* which extends over and encloses second stop block 62. Membrane 71 forms the outer wall of expansion chambers 63 and 64. The thickness and strength of membrane 71 is selected to provide sufficient strength to retract mid section 43 when the pressure on the expansion fluid has been withdrawn. Furthermore, the thickness and strength of membrane 71 is selected in order to provide somewhat greater resistance to the axial compressive forces than the resistance provided by the buckle points of the longitudinal bands 51–58. By providing a membrane of such strength, the buckle points will bend uniformly. This allows the expandable segment 40 to achieve an intermediate diameter as shown in FIGS. 2A and 2B wherein there has been uniform expansion of mid section 43 at an infinite number of intermediate diameters.

FIGS. 2A, 2B and 2C show radiographic contrast fluid 81 being introduced into the expanding mid section 43 in order to clearly mark the expanding section relative to the blood vessel or body canal. A means shown generally as 80 for introducing the contrast fluid 81 includes third passageway 23 formed in inner cylindrical member 20 and a port means 82 formed in inner cylindrical member 20 to provide fluid communication between the third passageway 23 and the expandable mid section 43. It is significant to note that the contrast fluid 81 is introduced under relatively low pressure, that is pressure less than one-half of pressures currently utilized to introduce the contrast fluid 81. Conventional balloon catheters of the prior art rely on pressurized contrast fluid to expand the balloon. In the present invention, expansion of the mid section 43 of expandable segment 40 is created by the axial compressive forces, and the contrast fluid 81 may be introduced at significantly lower pressures than known in the prior art. This has the distinct advantage of minimizing the risk of overexpanding an undesirable portion of a balloon and causing significant damage to the artery wall as well as minimizing the risks attendant with using relatively high pressure to expand the balloon catheter.

Figure 6:
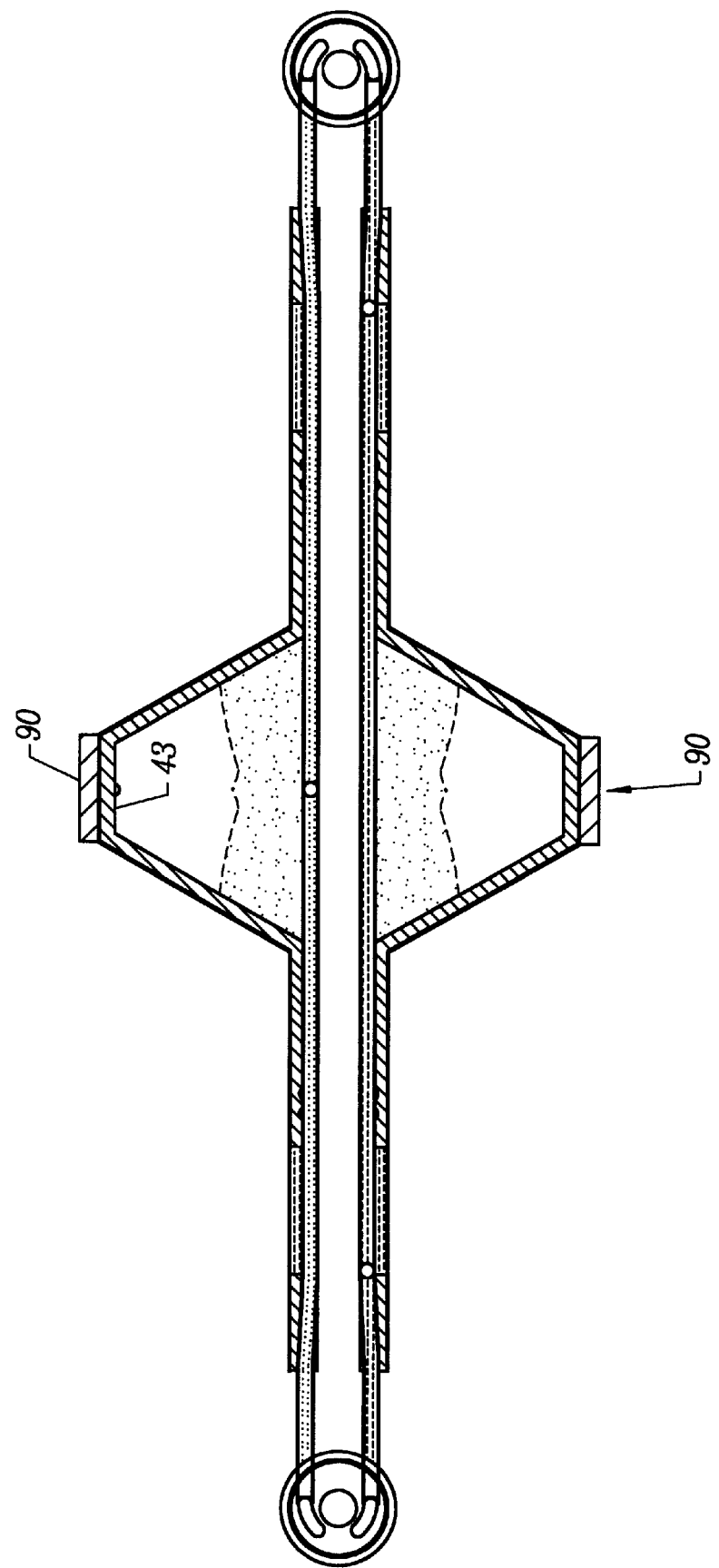
FIG. 6 shows the apparatus of FIGS. 1–5 as used with a stent.

FIG. 6 shows the embodiment of FIGS. 1–5 as used with a stent 90. The apparatus functions as described above with the exception that stent 90 is placed against the wall of the blood vessel or other body canal by the expanding mid section 43. When stent 90 is correctly in position, mid section 43 is retracted and the stent is left in place as is known in the prior art.

Figure 7:
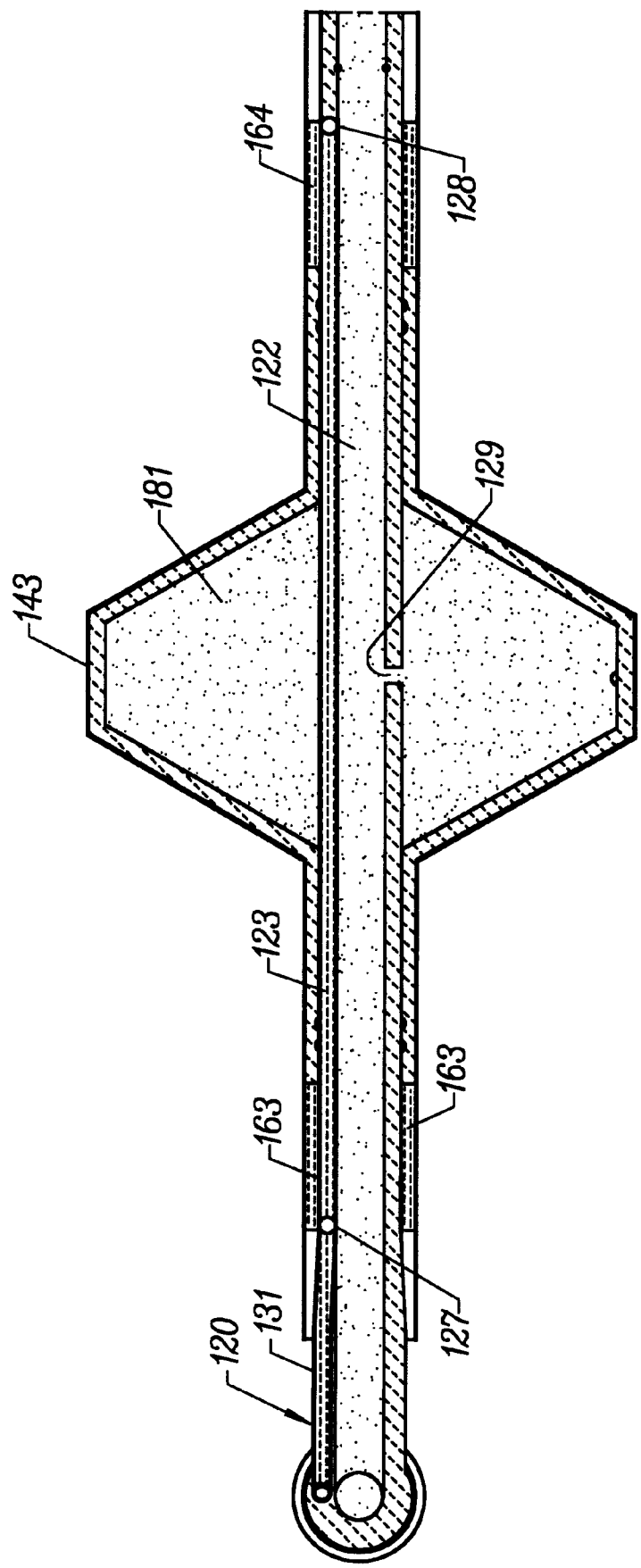
FIG. 7 is a side elevational view in section showing a second embodiment of the invention.

FIG. 7 shows an alternate embodiment of the invention. In this form of the invention, the inner elongated cylindrical member 120 has a central passageway 122. Central passageway 122 is used in this embodiment for the introduction of radiographic contrast fluid 181 through port 129 which extends through the side wall of cylinder 131 into the chamber formed by expanding mid section 143. This embodiment is primarily useful in body canals other than blood vessels, for example, the ureter, wherein a guide wire does not have to be used. Expansion chambers 163 and 164 are pressurized by expansion fluid flowing through passageway 123 formed in the wall of cylinder 131 and through port 127 into expansion chamber 163 and through port 128 into expansion chamber 164. The cylinder as shown in FIG. 7 would only require two passageways, one for introducing contrast fluid and one for introducing expansion fluid.

FIGS. 8A and 8B show further embodiments of the invention wherein two or more expandable segments are used in conjunction with each other (FIG. 8A) and multi-tasking (FIG. 8B). As shown in FIG. 8A, two expandable segments 240 and 340 are utilized together for the delivery and placement of stent 290. Expandable segments 240 and 340 function as the embodiment disclosed in FIGS. 1–5 above, including retractable membranes 271 and 371. In this embodiment, expandable sections 240 and 340 are placed in the blood vessel as desired by the physician, with stent 290 retracted against the retracted surface of the catheter. As expandable segments 240 and 340 are expanded simultaneously as described above, stent 290 is expanded by segments 240 and 340 until it contacts the vessel wall. Once proper contact has been established between stent 290 and the vessel wall, retraction membranes 271 and 371 retract the expandable segments 240 and 340 as described above, leaving stent 290 in place.

FIG. 8B shows a multi-tasking form of the invention. In this form of the invention, a first or lead member comprises expansion segments 440 and 540 which share a common elongated single retraction membrane 471. This lead segment is utilized to predilate an artery prior to stent placement, for example. The section is then retracted by membrane 471 and the catheter is then advanced so that the second section including expandable segments 640, 740 and 840 are prepositioned in the previously expanded portion of the artery. Expandable segments 640, 740 and 840 carry a stent 690 which, for example, may be 20 mm in length. Stent 690 may be placed in the predilated portion of the blood vessel or, alternately, the second stent 990, carried by expandable sections 940 and 1040, may be advanced and the shorter stent 990 (for example 10 mm in length) may be placed in the vessel.

The multi-tasking aspect of the invention as shown in FIG. 8B my also be utilized to introduce medicine to the wall of the vessel or other body canal through perforations in the retraction membranes 471, 671 and/or 971.

Figure 9:
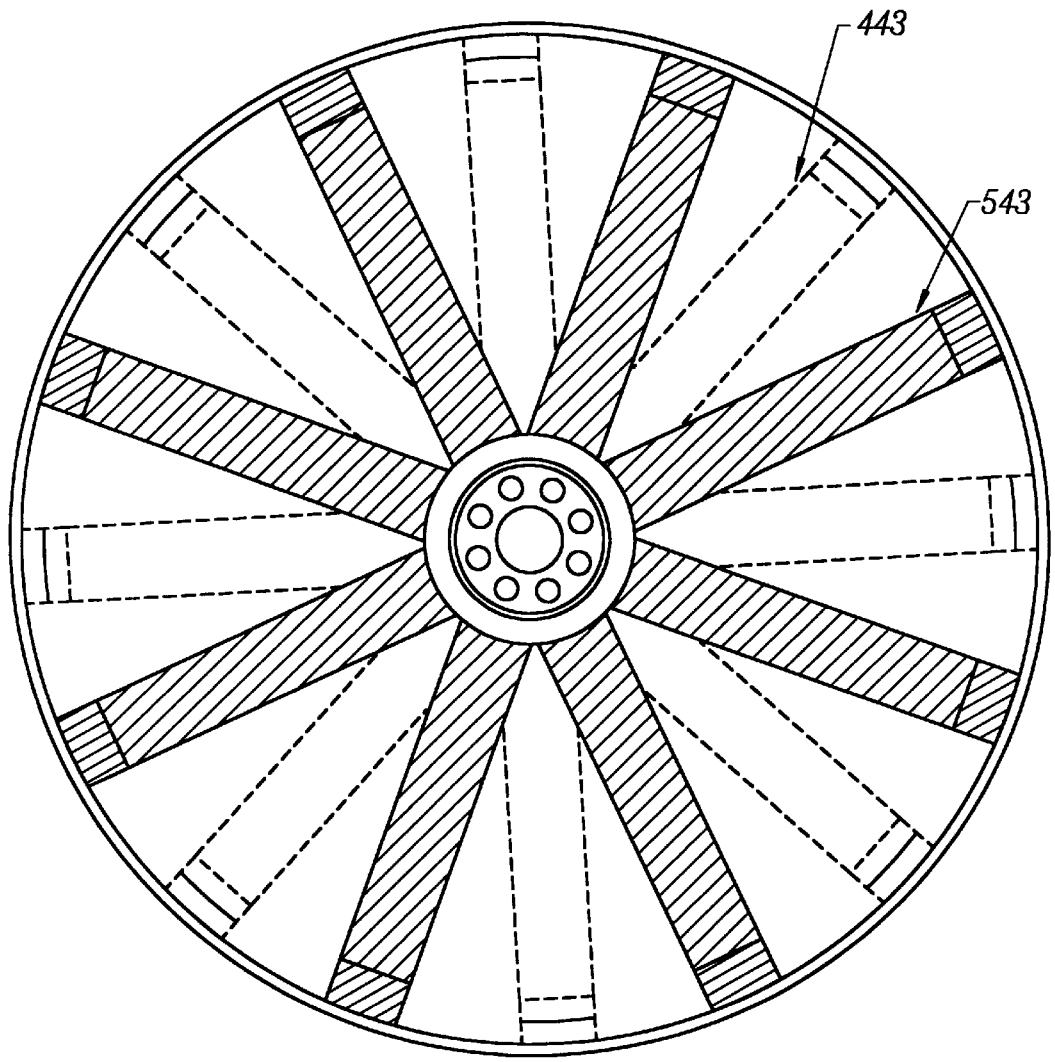
FIG. 9 is a sectional view on the line 9—9 of the embodiment shown in FIG. 8.

FIG. 9 is a sectional view on the line 9—9 of FIG. 8 and shows the expandable mid section 543 and in phantom 443 of expandable segments 540 and 440.

Figure 10A:
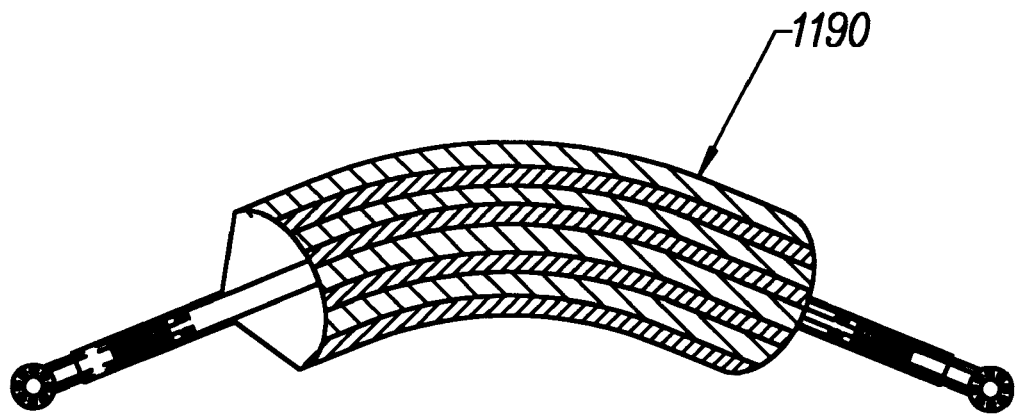
FIGS. 10A and 10B are schematic representations showing the invention as used in a curved blood vessel.
Figure 10B:
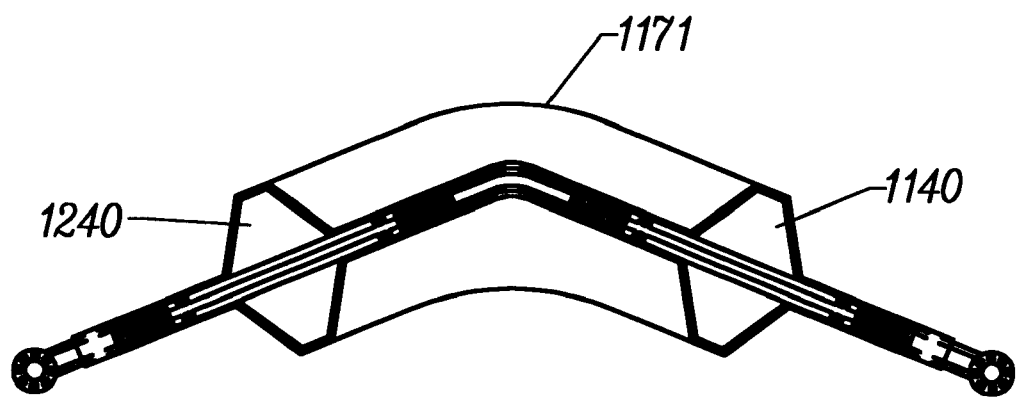

FIGS. 10A and 10B show schematically how the invention can be utilized in rather sharply curved blood vessels or other body canals. As shown in FIG. 10B, expandable segments 1140 and 1240 are used in conjunction with a single retractable membrane 1171. Expandable segments 1140 and 1240 are placed on opposite sides of a sharp curve in a blood vessel or other body canal and are then expanded. The flexible and resilient membrane 1171 expands in the sharply curved portion of the blood vessel or other body canal but not with the same degree of pressure as is necessary to expand prior art balloon catheters. In this fashion, the present invention may be utilized more safely in conjunction with sharply curved blood vessels in body canals. FIG. 10A shows essentially the same mechanism shown in FIG. 10B but with a stent 1190 being expanded by segments 1140 and 1240 and membrane 1171. Stent 1190 is expanded in the curved vessel with considerably less pressure than required by balloon catheters. This involves much less risk to the vessels.

Figure 11A:
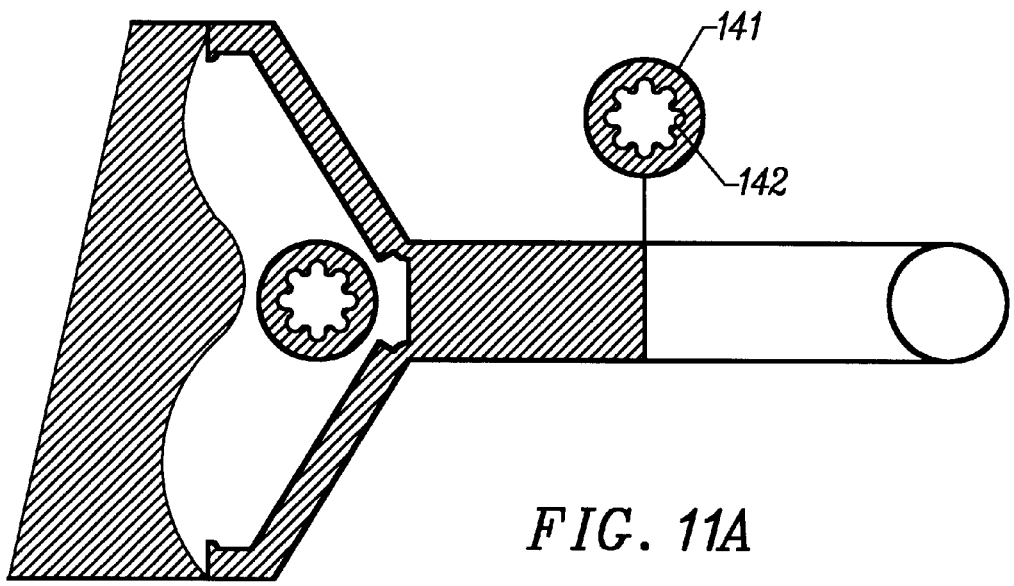
FIGS. 11A and 11B show the cross-sectional details of the inner elongated member and the outer sleeve portions of the invention.
Figure 11B:
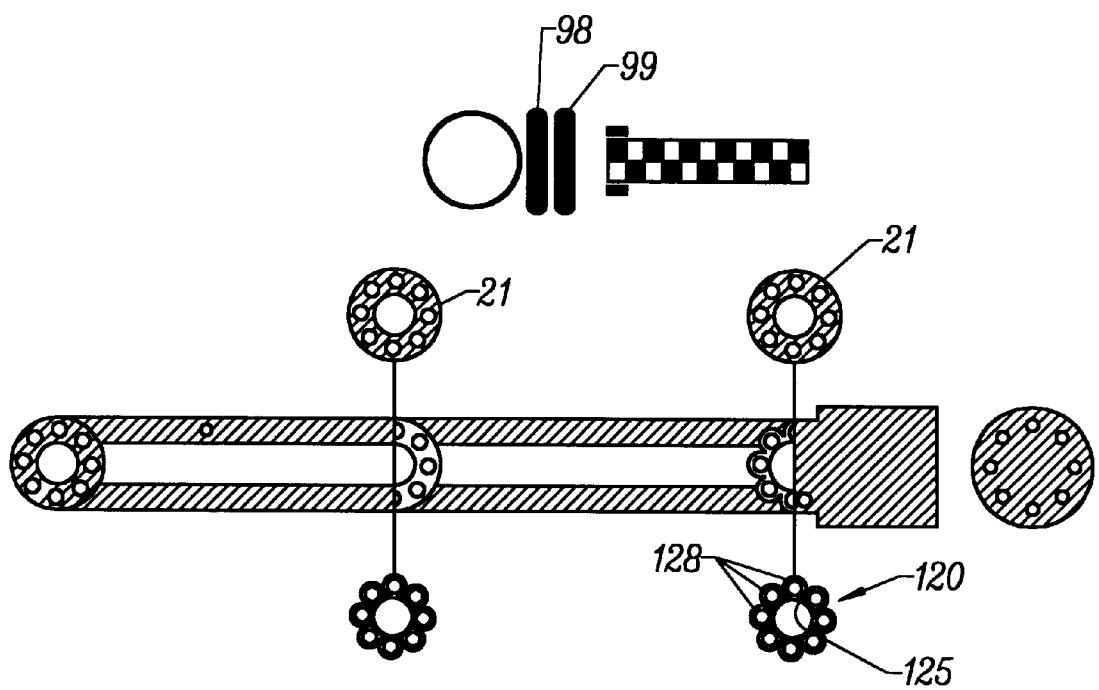

FIGS. 11A and 11B are schematic representations of alternate cross-sectional designs for the inner cylindrical member and the outer sleeve. FIG. 11B shows the circular cylinder 21 but also shows an alternate cylindrical member 120 which includes a central inner cylinder 125 surrounded by a plurality of eight smaller tubes 128. This alternate inner cylindrical member 120 is utilized with an outer sleeve 141 which has a scalloped internal surface 142 that slidably receives inner cylindrical member 120.

FIG. 11B also shows O-rings 98 and 99 which are placed between inner cylindrical member 20 and the outer sleeve 41 (see FIG. 2B) to seal the fluid expansion chambers as well as the chamber receiving contrast fluid 81.

Figure 12A:
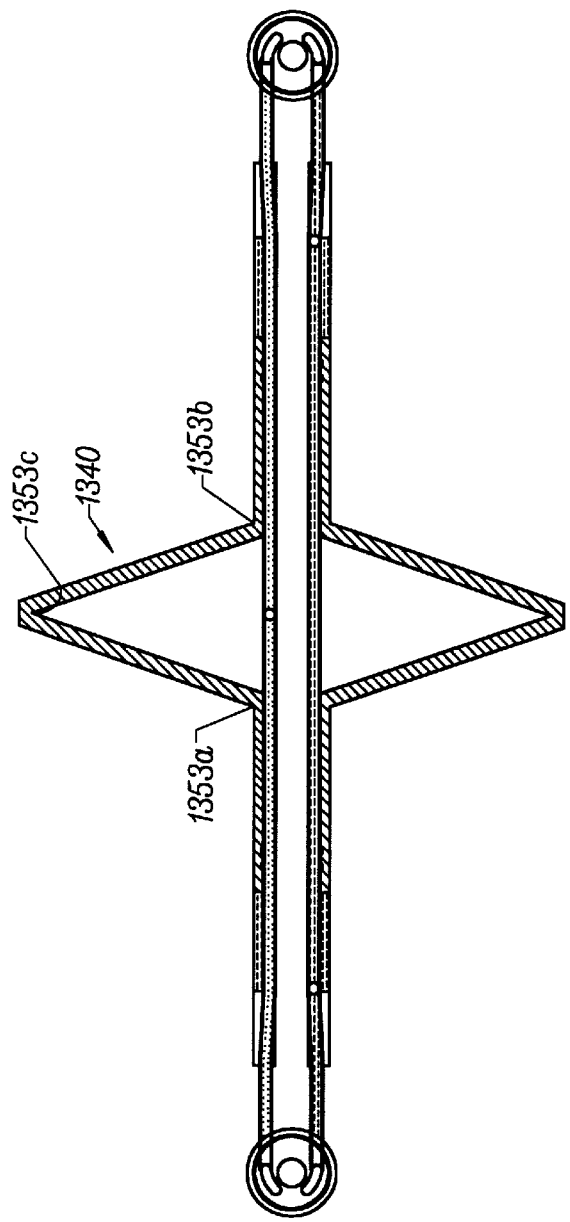
FIGS. 12A and 12B are schematic representations of alternate expandable segments.
Figure 12B:
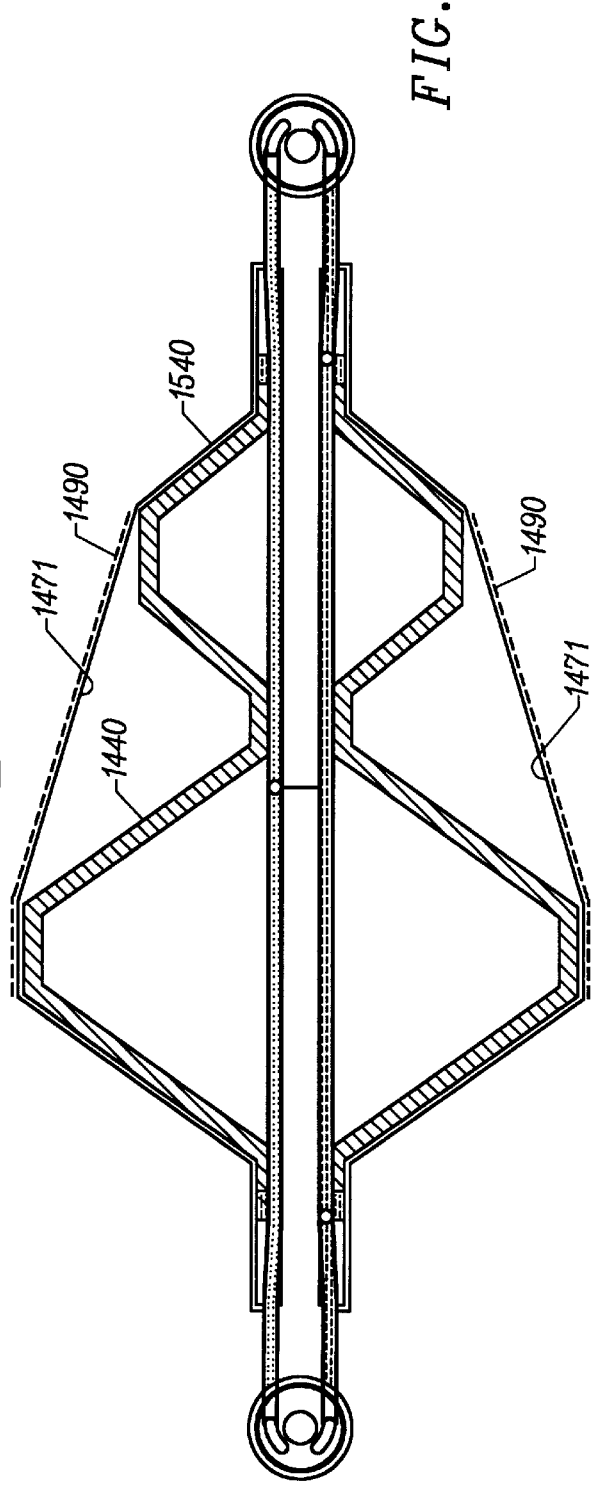

FIGS. 12A and 12B are schematic representations of alternate expandable segments. FIG. 12A shows an expandable segment 1340 having three buckle points 1353a, 1353b and 1353c. The use of three buckle points produces a triangular shaped expandable segment when viewed as shown in FIG. 12A.

FIG. 12B shows first and second expandable segments 1440 and 1540 wherein first segment 1440 expands a greater distance radially than second segment 1540. This feature provides a taper to membrane 1471 which has various advantageous uses in blood vessels and other body canals. As shown in FIG. 12B, the narrower segment 1540 is introduced into the blood vessel or other body canal ahead of the wider segment 1440. An optional tapered stent shown in phantom as 1490 may be implanted with this embodiment of the invention.

The buckle points discussed herein may be formed in several ways. First, metallic bands or composite material may be utilized and simply scored at desired buckle points. Where the bands connect to the inner ends of the proximal and distal sections, scoring is not necessary. Buckle points may also be provided by using different materials on either side of a proposed buckle point. Other techniques may also be used to create buckle points without departing from the invention.

As noted above, another feature of the present invention is that it may be utilized to form a plug in an artery to prevent blood reaching a downstream cancerous tumor.

Other various medical procedures could be used with the present invention. The most likely usable procedures have been identified herein, but the invention does have potential uses in gall bladder surgery, brain surgery and potential other uses. Various design modifications may be made to various components of the invention without departing from the spirit of the invention. For example, different cross sections may be used in the inner cylindrical member as well as in the outer sleeve, all without departing from the spirit of the invention.

What is claimed is:

1. A catheter having at least one expandable segment, said catheter capable of being inserted into a blood vessel or other body canal, and said segment being expandable at a selected location within said blood vessel or body canal, comprising:

an inner, elongated, cylindrical member, an expandable segment carried by the exterior surface of said inner, elongated, cylindrical member, said expandable segment including an outer sleeve, said sleeve having a proximal section, a mid section and a distal section, said mid section including a plurality of longitudinally extending bands, each of said bands having a plurality of buckle points so that, as compressive axial forces are applied which urge either or both of said proximal and distal sections toward said mid section, said bands bend at said buckle points in a predetermined manner to expand outwardly relative to said inner cylindrical member, expansion means for applying compressive axial forces to either or both of said proximal and distal sections, and retraction means for causing said mid section to retract, said means including a flexible, resilient membrane enclosing said mid section, wherein said flexible, resilient membrane expands with said mid section in response to application of axial compressive force by said expansion means, and wherein said flexible, resilient membrane causes said mid section to retract when said axial compressive forces are no longer applied.

2. The apparatus of claim 1 wherein said inner cylindrical member has a first passageway formed therein and extending along its longitudinal axis, and further comprising a guide wire adapted to extend through said first passageway.

3. The apparatus of claim 2 wherein said proximal and distal sections each have an inner end adjacent said mid section and an outer end, and wherein said expansion means comprises:

a stop block fixed to the outer surface of said inner member at a point near the outer end of either said proximal or distal section, means forming a fluid expansion chamber between said stop block and said outer end of either said proximal or distal section, a second passageway formed in said inner member, said passageway including a port formed in said inner member to provide fluid communication between said second passageway and said fluid expansion chamber, means for providing fluid to said second passageway, means for pressurizing said fluid in said second passageway and in said fluid expansion chamber to cause axial compression on either or both of said proximal and distal sections, thereby causing expansion of said mid section, and means for ceasing the application of pressure on the fluid in said second passageway to allow said mid section to retract.

4. The apparatus of claim 3 further comprising:

a third passageway formed in said inner member, said passageway including port means formed in said inner member to provide fluid communication between said third passageway and said expandable mid section, and, means for introducing radiographic contrast fluid under low pressure into said third passageway, whereby said low pressure contrast fluid fills the chamber formed by said mid section as it expands.

5. The apparatus of claim 2 wherein said proximal and distal sections each have an inner end adjacent said mid section and an outer end, and wherein said expansion means comprises:

first and second stop blocks fixed to the outer surface of said inner member at points near the outer ends of said proximal and distal sections, means forming first and second fluid expansion chambers between said stop blocks and said outer ends of said proximal and distal sections, a second passageway formed in said inner member, said passageway including a port formed in said inner member to provide fluid communication between said second passageway and said first and second fluid expansion chambers, means for providing fluid to said second passageway, means for pressurizing said fluid in said second passageway and in said fluid expansion chambers to cause axial compression on the outer ends of said proximal and distal sections, thereby causing expansion of said mid section, and means for ceasing the application of pressure on the fluid in said second passageway to allow said mid section to retract.

6. The apparatus of claim 3 wherein each of said bands of said mid section has four buckle points, including a first buckle point at the inner end of said proximal section, a second buckle point at the inner end of said distal section, and third and fourth buckle points located between said first and second buckle points.

7. The apparatus of claim 6 wherein each of said buckle points of said plurality of bands are coplanar and perpendicular to the longitudinal axis of said inner cylindrical member.

8. The apparatus of claim 1 having first and second expandable segments separated by a predetermined longitudinal distance and wherein said retraction means includes a single membrane enclosing said first and second expandable segments and extending along said predetermined longitudinal distance.

9. The apparatus of claim 8 wherein said first expandable segment expands a greater radial distance than said second expandable segment, whereby said membrane expands into a tapered shape.

10. The apparatus of claim 8 further comprising a stent extending over said membrane, said stent being expanded by said membrane as said expandable segments are expanded.

11. A catheter having first and second expandable segments, said catheter capable of being inserted into a blood vessel on a guide wire, and said segments being expandable at a selected location within said blood vessel, comprising:

an inner, elongated, cylindrical member, first and second expandable segments carried by the exterior surface of said inner, elongated, cylindrical member, said expandable segments each including an outer sleeve, said sleeve having a proximal section, a mid section and a distal section, said mid section including a plurality of longitudinally extending bands, each of said bands having a plurality of buckle points so that, as compressive axial forces are applied which urge either or both of said proximal and distal sections toward said mid section, said bands bend at said buckle points in a predetermined manner to expand outwardly relative to said inner cylindrical member, expansion means for applying compressive axial forces to both of said proximal and distal sections, and retraction means for causing each said mid section to retract, said means including a flexible, resilient membrane enclosing said first and second expandable segments, wherein said flexible, resilient membrane expands with said mid sections in response to application of axial compressive force by said expansion means, and wherein said flexible, resilient membrane causes said mid sections to retract when said axial compressive forces are no longer applied.

12. The apparatus of claim 11 wherein said inner cylindrical member has a first passageway formed therein and extending along its longitudinal axis, and further comprising a guide wire adapted to extend through said first passageway.

13. The apparatus of claim 12 further comprising:

a third passageway formed in said inner member, said passageway including port means formed in said inner member to provide fluid communication between said third passageway and said expandable mid sections, and, means for introducing radiographic contrast fluid under low pressure into said third passageway, whereby said low pressure contrast fluid fills the chambers formed by said mid sections as each expands.

14. The apparatus of claim 13 wherein each of said proximal and distal sections has an inner end adjacent said mid section and an outer end, and wherein said expansion means comprises:

first and second stop blocks fixed to the outer surface of said inner member at points near the outer ends of said proximal and distal sections, means forming first and second fluid expansion chambers between said stop blocks and said outer ends of both said proximal and distal sections, a second passageway formed in said inner member, said passageway including ports formed in said inner member to provide fluid communication between said second passageway and both pairs of first and second fluid expansion chambers, means for providing fluid to said second passageway, means for pressurizing said fluid in said second passageway and in said fluid expansion chambers to cause axial compression on the outer ends of said proximal and distal sections, thereby causing expansion of each of said mid sections, and means for ceasing the application of pressure on the fluid in said second passageway to allow said mid section to retract.

15. The apparatus of claim 14 further comprising a stent carried by said catheter, said stent extending over said flexible resilient membrane, said stent being expanded by said membrane as said expandable segments are expanded.

* * * * *